US006186972B1

(12) United States Patent
Nelson et al.

(10) Patent No.: US 6,186,972 B1
(45) Date of Patent: Feb. 13, 2001

(54) METHODS AND APPARATUS FOR TREATING ISCHEMIC HEART DISEASE BY PROVIDING TRANSVENOUS MYOCARDIAL PERFUSION

(76) Inventors: James A. Nelson, 5655 NE. Windermere Rd., Seattle, WA (US) 98105; Ascher Shmulewitz, 4338 W. Mercer Way, Mercer Island, WA (US) 98040; John Burton, 15460 Wing Lake Dr., Minnetonka, MN (US) 55345

(*) Notice: Under 35 U.S.C. 154(b), the term of this patent shall be extended for 0 days.

(21) Appl. No.: 09/208,807

(22) Filed: Dec. 9, 1998

Related U.S. Application Data

(63) Continuation-in-part of application No. 08/929,076, filed on Sep. 15, 1997, which is a continuation-in-part of application No. 08/798,700, filed on Feb. 12, 1997, now Pat. No. 5,824,071, which is a division of application No. 08/714,466, filed on Sep. 16, 1996, now Pat. No. 5,655,548.

(51) Int. Cl.$^7$ .................................................. A61B 19/00
(52) U.S. Cl. .............................. 604/8; 128/898; 606/194
(58) Field of Search .......................... 128/898; 604/282, 604/7, 8, 9, 93, 916; 606/15, 7, 194; 623/1, 3, 11.11; 600/16

(56) References Cited

U.S. PATENT DOCUMENTS

| | | | | |
|---|---|---|---|---|
| 4,302,854 | * | 12/1981 | Runge | 623/3 |
| 4,382,445 | * | 5/1983 | Sommers | 604/8 |
| 4,712,551 | * | 12/1987 | Rayhanabad | 604/8 X |
| 4,995,857 | * | 2/1991 | Arnold | 623/3 X |

(List continued on next page.)

FOREIGN PATENT DOCUMENTS

| | | |
|---|---|---|
| WO97/13463 | 4/1997 | (WO) . |
| WO97/13471 | 4/1997 | (WO) . |

OTHER PUBLICATIONS

Mohl, Werner, "Coronary Sinus Interventions: From Concept to Clinics," *Journal of Cardiac Surgery*, vol. 2, No. 4, (Dec. 1987), pp. 467–493.

*Cardiac Catheterization and Angiography*, William Grossman, Ed., Lea & Febiger, Philadelphia (1980), pp. 63–69.

Ihnken, Kai et. al., "The Safety of Simultaneous Arterial and Coronary Sinus Perfusion: Experimental Background and Initial Clinical Results," *Journal of Cardiac Surgery*, vol. 9, No. 1, (Jan. 1994), pp. 15–25.

Ihnken, Kai et al., "Simultaneous Arterial and Coronary Sinus Cardioplegic Perfusion: an Experimental and Clinical Study," *The Thoracic and Cardiovascular Surgeon*, vol. 42, (Jun. 1994), pp. 141–147.

Iguidbashian, John P. et al., "Advantages of Continuous Noncardioplegic Warm Blood Retrograde Perfusion over Antegrade Perfusion During Proximal Coronary Anastomoses," *Journal of Cardiac Surgery*, vol. 10, No. 1,(Jan. 1995), pp. 27–31.

(List continued on next page.)

*Primary Examiner*—Vincent Millin
*Assistant Examiner*—Kelly O'Hara
(74) *Attorney, Agent, or Firm*—Nicola A. Pisano; Fish & Neave

(57) ABSTRACT

Methods and apparatus for supplying retrograde perfusion of chronically ischemic myocardium by forming one or more transmural passageways between a cardiac chamber and the coronary venous vasculature. The placement, size and number of the passageways are selected, and portions of the venous vasculature or coronary ostium optionally partially or completely occluded, to maintain a parameter related to the pressure attained in the venous vasculature to a value less than a predetermined value.

20 Claims, 5 Drawing Sheets

U.S. PATENT DOCUMENTS

| | | | |
|---|---|---|---|
| 5,287,861 | 2/1994 | Wilk | 128/898 |
| 5,352,240 * | 10/1994 | Ross | 623/1 X |
| 5,380,316 | 1/1995 | Aita et al. | 606/7 |
| 5,389,096 | 2/1995 | Aita et al. | 606/15 |
| 5,409,019 | 4/1995 | Wilk | 128/898 |
| 5,429,144 | 7/1995 | Wilk | 128/898 |
| 5,445,600 * | 8/1995 | Abdulla | 604/9 |
| 5,456,714 * | 10/1995 | Owen | 604/8 X |
| 5,549,581 | 8/1996 | Lurie et al. | 604/282 |
| 5,607,465 * | 3/1997 | Camilli | 623/1 X |

OTHER PUBLICATIONS

Lichtenstein, Samuel V. et al., "Warm Retrograde Cardioplegia: Protection of the Right Ventrical in Mitral Valve Operations," *The Journal of Thoracic and Cardiovascular Surgery,* vol. 104, No. 2, (Aug. 1992), pp. 374–380.

Ropchan, Glorianne V. et al., "Salvage of Ischemic Myocardium by Nonsynchronized Retroperfusion in the Pig," *The Journal of Thoracic and Cardiovascular Surgery,* vol. 104, No. 3, (Sep. 1992), pp. 619–625.

Franz, N. et al., "Transfemoral Balloon Occlusion of the Coronary Sinus in Patients with Angina Pectoris," *Radiologia Diagnostica,* 31(1), (1990), pp. 35–41. (Abstract).

Kuraoka, S. et al., "Antegrade or Retrograde Blood Cardioplegic Method: Comparison of Postsurgical Right Ventricular Function and Conduction Disturbances," *Japanese Journal of Thoracic Surgery,* 48(5), (May 1995), pp. 383–386. (Abstract).

Lincoff, A.M. et al., "Percutaneous Support Devices for High Risk or Complicated Coronary Angioplasty," *Journal of the American College of Cardiology,* 17(3), (Mar. 1991), pp. 770–780.

Rudis, E. et al., "Coronary Sinus Ostial Occlusion During Retrograde Delivery of Cardioplegic Solution Significantly Improves Cardioplegic Distribution and Efficacy," *Journal of Thoracic and Cardiovascular Surgery,* 109(5), (May 1995), pp. 941–946.

Huang, A.H. et al., "Coronary Sinus Pressure and Arterial Venting Do Not Affect Retrograde Cardioplegia Distribution," *Annals of Thoracic Surgery,* 58(5), (Nov. 1994), pp. 1499–1504.

Tokunaga, S., et al., "Left Ventricular–Coronary Sinus Shunt Through a Septal Aneurysm After Mitral Valve Replacement," *Annals of Thoracic Surgery,* 59(1), (Jan. 1995), pp. 224–227.

Goldman, Alfred, M.D. et al., "Experimental Methods for Producing a Collateral Circulation to the Heart Directly from the Left Ventrical," *Journal of Thoracic Surgery,* (Mar. 1956), pp. 364–374.

Massimo, C., M.D. et al., "Myocardial Revascularization by a New Method of Carrying Blood Directly from the Left Ventricular Cavity into the Coronary Circulation," *Journal of Thoracic Surgery,* (Aug. 1957), pp. 257–264.

Munro, Ian, M.D. et al., "The Possibility of Myocardial Revascularization by Creation of a Left Ventriculocoronary Artery Fistula," *Journal of Thoracic and Cardiovascular Surgery,* 58(1), (Jul. 1969), pp. 25–32.

* cited by examiner

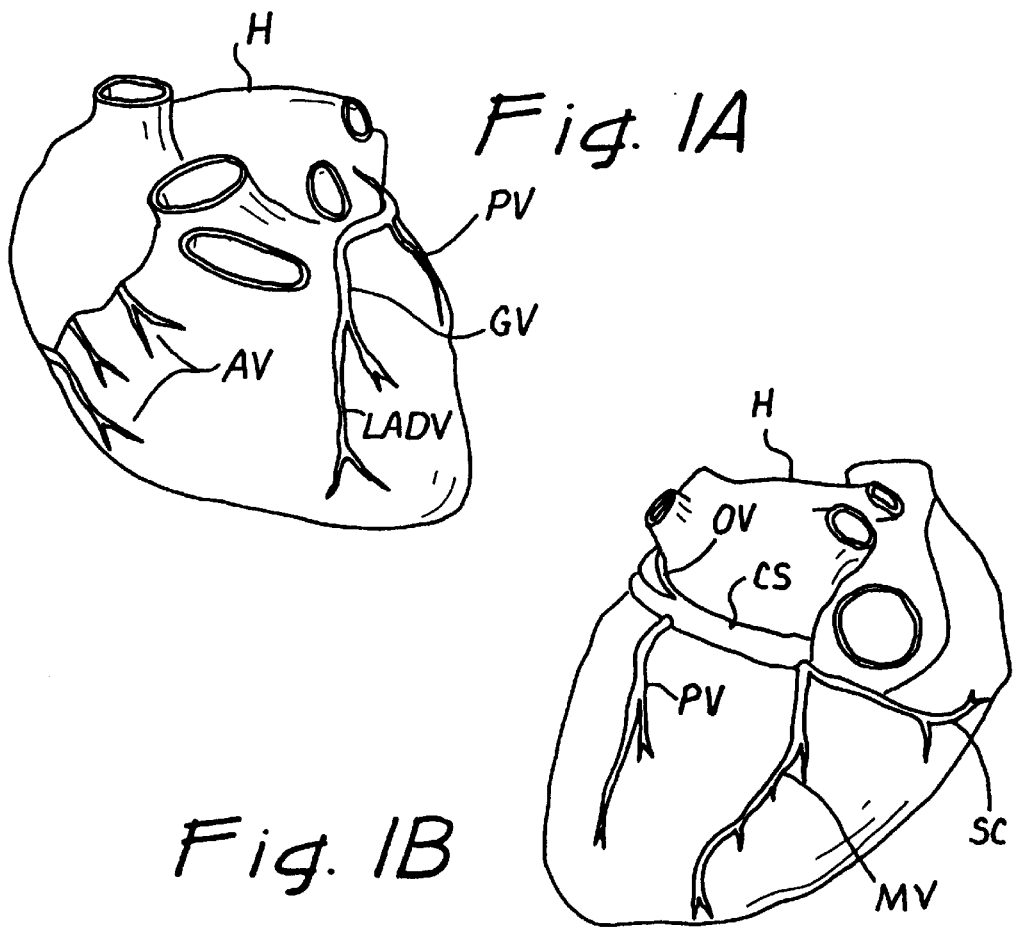
Fig. 1A
Fig. 1B
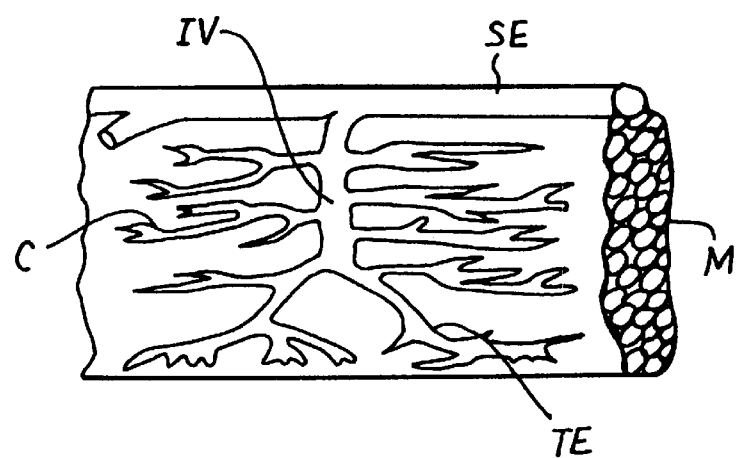
Fig. 2

METHODS AND APPARATUS FOR TREATING ISCHEMIC HEART DISEASE BY PROVIDING TRANSVENOUS MYOCARDIAL PERFUSION

REFERENCE TO RELATED APPLICATIONS

This application is a continuation-in-part of U.S. patent application Ser. No. 08/929,076, filed Sep. 15, 1997, which is a continuation-in-part of U.S. patent application Ser. No. 08/798,700, filed Feb. 12, 1997, which is a division of U.S. patent application Ser. No. 08/714,466, filed Sep. 16, 1996, now U.S. Pat. No. 5,655,548.

FIELD OF THE INVENTION

The present invention relates generally to methods and apparatus for treating ischemic heart disease, and more particularly, cases involving diffuse coronary atherosclerosis, by perfusing the myocardium with oxygenated blood from a cardiac chamber, such as the left atrium or left ventricle, using the coronary venous vasculature.

BACKGROUND OF THE INVENTION

The cardiac blood perfusion system is composed of two coronary arterial vessels, the left and right coronary arteries, which perfuse the myocardium from the epicardial surface inward towards the endocardium. Blood flows through the capillary systems into the coronary veins, and into the right atrium via the coronary sinus. Two additional systems, the lymphatic and the Thebesian veins, drain a portion of the blood perfused into the myocardium directly into the heart chambers. The venous system has extensive collaterals and, unlike the coronary arteries, does not occlude in atherosclerotic disease.

A number of techniques have been developed to treat ischemic heart disease caused, for example, by atherosclerosis. These treatments have improved the lives of millions of patients worldwide, yet for certain classes of patients current technology offers little relief or hope.

Best known of the current techniques is coronary artery bypass grafting, wherein a thoracotomy is performed to expose the patient's heart, and one or more coronary arteries are replaced with saphenous veins. In preparation for the bypass grafting, the heart is arrested using a suitable cardioplegia solution, while the patient is placed on cardiopulmonary bypass (i.e., a heart-lung machine) to maintain circulation throughout the body during the operation. Typically, a state of hypothermia is induced in the heart muscle during the bypass operation to reduce oxygen utilization, thereby preserving the tissue from further necrosis. Alternatively, the heart may be perfused throughout the operation using either normal or retrograde flow through the coronary sinus, with or without hypothermia. Once the bypass grafts are implanted, the heart is resuscitated, and the patient is removed from cardiopulmonary bypass.

Drawbacks of conventional open heart surgery are that such surgery is time-consuming and costly, involves a significant risk of mortality, requires a lengthy period of recuperation, and involves significant discomfort to the patient.

As a result of the foregoing drawbacks, techniques have been developed that permit coronary bypass grafting to be performed endoscopically, i.e., using elongated instruments inserted through incisions located between the ribs. A drawback of these keyhole techniques, however, is that they can be used only for coronary arteries that are readily accessible, and not, for example, those located posteriorly.

Alternatively, techniques such as percutaneous transluminal angioplasty ("PTA") have been developed for reopening arteries, such as the coronary arteries, that have become constricted by plaque. In these techniques, a balloon catheter is typically inserted into the stenosis and then inflated to compress and crack the plaque lining the vessel, thereby restoring patency to the vessel. Additionally, a vascular prosthesis, commonly referred to as a "stent," may be inserted transluminally and expanded within the vessel after the angioplasty procedure, to maintain the patency of the vessel after the PTA procedure.

U.S. Pat. No. 5,409,019 to Wilk describes an alternative method of creating a coronary bypass, wherein a valve-like stent is implanted within an opening formed between a coronary artery and the left ventricle. The patent describes that the stent may be implanted transluminally.

A drawback of the foregoing transluminal approaches is that the treatment device, e.g., the balloon catheter or the stent delivery system described in U.S. Pat. No. 5,409,019, must be inserted in the vessel before it can be expanded. Occasionally, a stenosis may occlude so much of a vessel that there is insufficient clearance to advance a guidewire and catheter within the stenosis to permit treatment. In addition, arterial blockages treatable using PTA techniques are restricted to the portions of the anatomy where such techniques can be beneficially employed.

Moreover, the above-described techniques—both open-surgery and transluminal—are useful only where the stenosis is localized, so that the bypass graft or PTA procedure, when completed, will restore near normal blood flow to the effected areas. For certain conditions, however, such as diffuse atherosclerosis, blockages may exist throughout much of the coronary artery system. In such situations, treatment, if possible, typically involves heart transplant.

Historically, attempts have been made to treat diffuse blockages of the coronary arterial system by introducing retrograde flow through the coronary venous system. As described, for example, in W. Mohl, "Coronary Sinus Interventions: From Concept to Clinics," *J. Cardiac Surg.*, Vol. 2, pp. 467–493 (1987), coronary venous bypass grafts have been attempted wherein the coronary sinus was ligated, and a shunt was implanted between a cardiac vein and the aorta, thus providing permanent retrograde perfusion. It was observed that such bypass grafts resulted in underperfusion of certain regions of the myocardium and edema of the venous system. Consequently, as reported in the aforementioned Mohl article, these techniques are rarely used in cardiac surgery, while permanent retroperfusion is never used in interventional cardiology.

Despite disenchantment with retroperfusion via the coronary sinus for long-term perfusion of the myocardium, retrograde coronary venous perfusion is now routinely used in coronary interventional procedures to perfuse the heart during the procedure. Franz et al., in "Transfemoral Balloon Occlusion of the Coronary Sinus in Patients with Angina Pectoris," *Radiologia Diagnostica*, 31(1), pp. 35–41 (1990), demonstrated the possibility of transfemoral coronary sinus balloon occlusion in patients with angina pectoris. In recent years, the use of retrograde arterial perfusion of blood through the coronary sinus has gained wide acceptance as a technique to preserve the myocardium during bypass procedures (Kuraoka et al., "Antegrade or Retrograde Blood Cardioplegic Method: Comparison of Post-Surgical Right Ventricular Function and Conduction Disturbances," *Japanese J. Thoracic Surg.*, 48(5), pp. 383–6, (1995)) and during high risk or complicated angioplasty (Lincoff et al., "Percutaneous Support Devices for High Risk or Complicated Coronary Angioplasty," *J. Am. Coll. Cardiol.,* 17(3), pp. 770–780 (1991)). This perfusion technique allows continuous warm cardioplegia and allows the flow of blood through the coronary venous bed distal to the occlusion.

It has also been reported by Rudis et al. in "Coronary Sinus Ostial Occlusion During Retrograde Delivery of Cardioplegic Solution Significantly Improves Cardioplegic Distribution and Efficiency," *J. Thoracic & Cardiovasc. Surg.,* 109(5), pp. 941–946 (1995), that retrograde blood flow through the coronary venous system may be augmented by coronary ostial occlusion. In this case, blood flows retrograde to the myocardium and drainage is through the lymphatic system and the Thebesian veins. Huang et al., in "Coronary Sinus Pressure and Arterial Venting Do Not Affect Retrograde Cardioplegic Distribution," *Annals Thoracic Surg.,* 58(5), pp. 1499–1504, that flow through the myocardium is not significantly effected by coronary arterial occlusion and venting, or by increases in coronary perfusion pressure. Also, K. Ihnken et al., in "Simultaneous Arterial and Coronary Sinus Cardioplegic Perfusion, an Experimental and Clinical Study," *Thoracic and Cardiovascular Surgeon,* Vol. 42, pp.141–147 (June 1994), demonstrated the benefits of using simultaneous arterial and coronary sinus perfusion during cardiac bypass surgery, with no ventricular edema, lactate production, lipid peroxidation, or effect on post-bypass left ventricular elastance or stroke work index.

For a large number of patients in the later phases of ischemic heart disease, and particularly diffuse atherosclerotic disease, current technology offers little relief or hope. In such instances, humanely extending the patient's life for additional months may provide significant physical and emotional benefits for the patient.

In view of the foregoing, it would be desirable to provide methods and apparatus for treating ischemic heart disease in a wider range of open surgical and interventional cardiology procedures.

It also would be desirable to provide methods and apparatus for providing transvenous myocardial perfusion that reduce the risk of edema within the venous system.

It would further be desirable to provide methods and apparatus that enable patients suffering from the later phases of diffuse ischemic heart disease to experience renewed vigor, reduced pain and improved emotional well-being during the final months or years of their lives.

SUMMARY OF THE INVENTION

In view of the foregoing, it is an object of this invention to provide methods and apparatus for treating ischemic heart disease in a wider range of open surgical and interventional cardiology procedures.

It is another object of the present invention to provide methods and apparatus for providing transvenous myocardial perfusion that reduce the risk of edema within the venous system.

It is a further object of this invention to provide methods and apparatus that enable patients suffering from the later phases of diffuse ischemic heart disease to experience renewed vigor, reduced pain and improved emotional well-being during the final months or years of their lives, or which provides critical time during which a donor heart, for example, may be located for transplantation.

In accordance with the present invention, methods and apparatus are provided for forming one or more transmural passageways between a cardiac chamber, such as left atrium or the left ventricle, and the coronary venous vasculature, thereby enabling retrograde perfusion of the myocardium.

In accordance with a first embodiment of the methods and apparatus, suitable for use in percutaneous applications, a catheter is advanced through the coronary ostium (in the right atrium) and positioned within a selected portion of the venous vasculature. Access to the right atrium may be established using either the subclavian veins and the superior vena cava or an approach through a femoral vein. One or more transmural passageways are then formed between the selected portions of the venous system and the left atrium or left ventricle using the catheter.

The placement, number and/or size of the transmural passageways is selected to provide a pressure differential sufficient to cause retrograde perfusion in the venous vasculature, but without leading to edema of the venous system. Optionally, the coronary ostium and/or portions of the venous vasculature proximal of the transmural channels, or collateral vessels, may be partially or fully occluded. Alternatively, or in addition, a stent may be deployed in the transmural passageway to retain patency.

BRIEF DESCRIPTION OF THE DRAWINGS

Further features of the invention, its nature and various advantages will be more apparent from the accompanying drawings and the following detailed description of the preferred embodiments.

FIGS. 1A and 1B are partial sternocoastal and diaphragmatic surface views of a human heart illustrating the coronary venous vasculature;

FIG. 2 is a sectional view of the myocardium, showing certain components of the cardiac venous system;

DETAILED DESCRIPTION OF THE INVENTION

Figure 3:
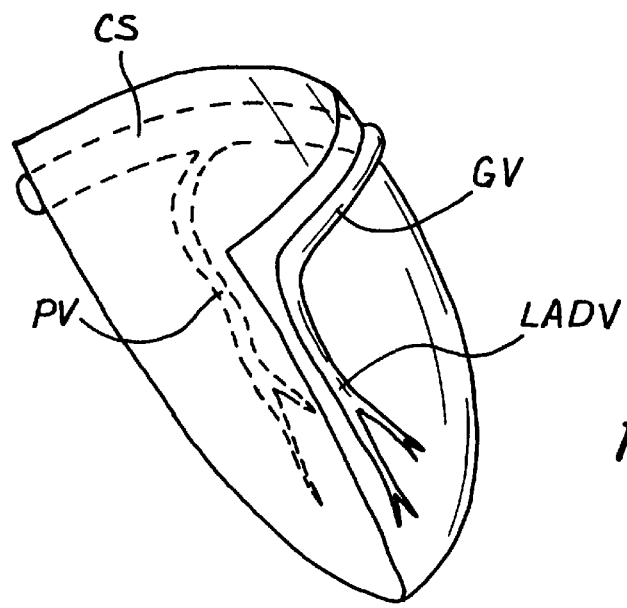
FIG. 3 is a perspective view from inside the left ventricle showing the spatial relationships between the portions of the coronary venous vasculature overlying the left ventricle.

The present invention relates generally to methods and apparatus for use in percutaneous and intraoperative procedures for providing transvenous myocardial perfusion for patients suffering from diffuse forms of ischemic heart disease, such as atherosclerosis. In accordance with the present invention, the apparatus forms one or more transmural passageways between a cardiac chamber (e.g., the left atrium or the left ventricle) and the coronary venous vasculature (i.e., coronary sinus and connecting cardiac veins) to permit blood ejected from the cardiac chamber to enter the venous system and perfuse the myocardium. Hereinafter, such transmural passageways are referred to as "veno-ventricular passageways."

Further in accordance with the methods and apparatus of the present invention, a parameter associated with the pressure attained in the venous system preferably is limited to a value, less than a predetermined value, to prevent edema of the venous system. This is accomplished by selecting the size, placement and number of the veno-ventricular passageways to maintain a peak pressure attained in the venous system to less than about 40 mm Hg.

This description of the present invention is organized as follows: First, the anatomy of the heart and coronary venous system relevant to the present invention are described. A heart, illustratively treated with methods of, and apparatus constructed in accordance with, the present invention, is then described. This is followed by a description of the components of various embodiments of the apparatus of the present invention, and operation thereof.

Referring to FIGS. 1A, 1B and 2, the coronary venous vasculature of human heart H and a model of the myocardial veins, respectively, are described. The venous system comprises coronary sinus CS that provides drainage for great cardiac vein GV, left anterior descending cardiac vein LADV, middle cardiac vein MV, the oblique vein of the left atrium OV, the posterior vein of the left ventricle PV and small cardiac vein SC. Deoxygenated blood flowing into coronary sinus CS exits via coronary ostium CO into the right atrium. The venous system further includes anterior cardiac veins AV that drain directly into the right atrium.

With respect to FIG. 2, myocardium M includes a lattice of capillaries C that drain deoxygenated blood into intramyocardial veins IV. From intramyocardial veins IV, a fraction of the blood drains into the cardiac veins via subepicardial veins SE, while the remainder drains through the Thebesian veins TE directly into the atrial and ventricular cavities. It has been reported in healthy human hearts that approximately 70% of the deoxygenated blood is drained through the coronary sinus, while the remaining 30% is drained in about equal proportions into the left and right atria and ventricles via the lymphatic system and the Thebesian veins. It has likewise been reported that when individual components of the venous system (i.e., the coronary sinus, lymphatic system and Thebesian veins) are occluded, the flow redistributes itself through the remaining unoccluded channels.

The coronary arteries are formed of resilient tissue fibers that withstand the pressures typically generated in the left ventricle during cardiac systole, generally up to a peak pressure of about 120 mm Hg. By contrast, the tissue fibers of the cardiac venous system are much less resilient than those of the coronary arterial system, with pressures in the coronary sinus generally not exceeding 6–10 mm Hg. Consequently, it is believed that chronic retroperfusion of the myocardium via the coronary sinus may lead to edema of the cardiac veins, which are generally believed to be incapable of sustaining pressures above about 40 mm Hg.

In FIG. 3 the relative positions of portions of the coronary venous vasculature are shown with respect to the left ventricle, i.e., those vessels disposed on the epicardium directly overlying the left ventricle. More specifically, portions of the coronary sinus CS, the great cardiac vein GV, the left anterior descending cardiac vein LADV, and posterior vein of the left ventricle PV, overlie the left ventricle. The spatial relationships of the coronary sinus and veins depicted in FIG. 3 are intended to be merely illustrative, since normal hearts can show a considerable degree of variation.

In accordance with the principles of the present invention, one or more veno-ventricular passageways are formed through the myocardium between a cardiac chamber, such as the left atrium or left ventricle, and the overlying portions of the venous vasculature depicted in FIG. 3. The passageways are formed by a device that preferably coagulates the tissue defining the passageway, so that the passageway is kept patent by flow passing therethrough. Alternatively, the passageway may be lined with a stent. In either case, the placement, size and/or number of passageways is selected to ensure that certain criterion (e.g., a pressure parameter) attained in the venous system is less than some predetermined value.

Optionally, upon completion of the formation of the veno-ventricular passageways, a plug may be disposed either in the coronary sinus, just proximally of the veno-ventricular passageway (in the context of the cardiac veins, the proximal direction is that closest to the coronary ostium), or both, to partially or completely occlude the vessel. In this way, it is expected that a backpressure may be induced in the venous system so that oxygenated blood ejected by the cardiac chamber into the venous system flows in a retrograde direction, thereby perfusing a portion of the myocardium.

Figure 4:
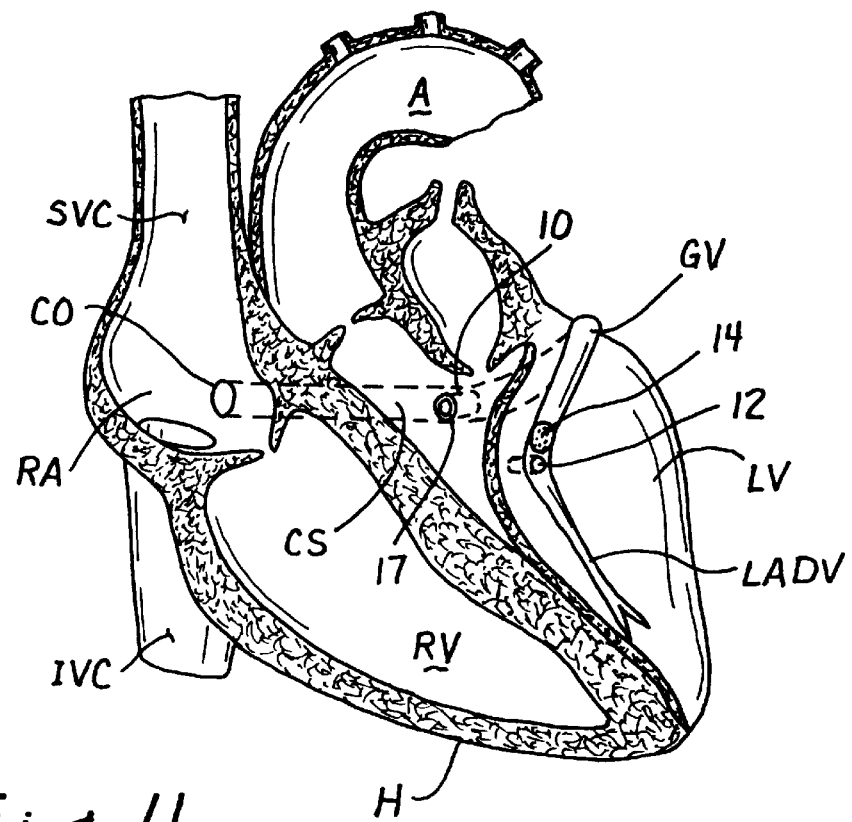
FIG. 4 is a view of a human heart, partly in section, treated using the methods and apparatus of the present invention.

Referring now to FIG. 4, a human heart treated with the methods and apparatus of the present invention is described. FIG. 4 depicts human heart H partly in cross-section, within which apparatus of the present invention has been utilized in accordance with the methods described hereinafter. Human heart H includes superior vena cava SVC and inferior vena cava IVC communicating with right atrium RA, right ventricle RV, left atrium LA, left ventricle LV, and aorta A (for clarity, the pulmonary artery has been omitted). From the posterior to anterior regions of the heart H, coronary sinus CS enters the right atrium RA via the coronary ostium CO, passes behind heart H (shown in dotted outline), and connects to great cardiac vein GV and left anterior descending vein LADV.

In FIG. 4, heart H is shown after completion of the treatment, and includes veno-ventricular passageway 10 formed between left ventricle LV and the left anterior descending cardiac vein LADV and veno-ventricular passageway 12 formed between the left ventricle and coronary sinus CS. Plug 14 is lodged just proximally of the outlet of passageway 12 in left anterior descending cardiac vein LADV to segregate that portion of the vein from the great cardiac vein GV. Plug 14 either partially, progressively, or fully, occludes the vessel proximally of the passageway 12. During cardiac systole and the early phases of cardiac diastole, blood is ejected through passageways 10 and 12 and into the respective portions of the venous vasculature, where it perfuses the myocardium. Passageway 10 is fitted with an optional stent 17 which retains the patency of passageway 10.

Figure 5A:
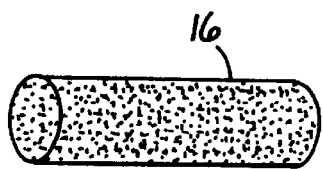
FIGS. 5A to 5C are illustrative embodiments of plugs for partially or fully occluding the coronary ostium or portions of the coronary vasculature.
Figure 5B:
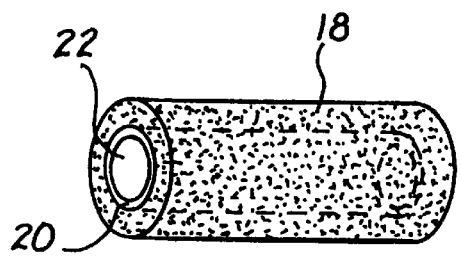
Figure 5C:
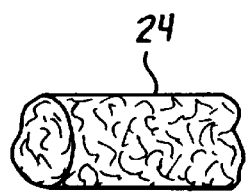
Figure 6A:
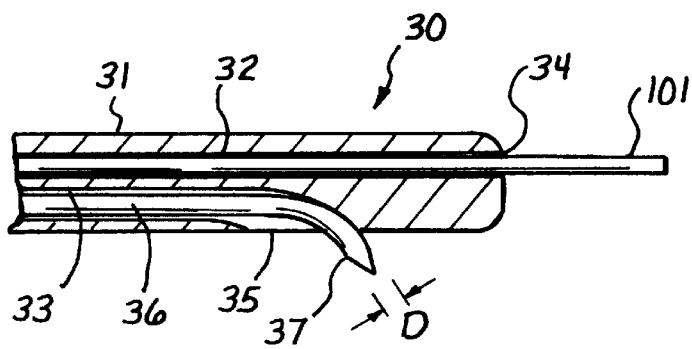
FIGS. 6A and 6B are sectional views illustrative catheters for forming transmural passageways between a portion of the coronary venous vasculature and a cardiac chamber.
Figure 6B:
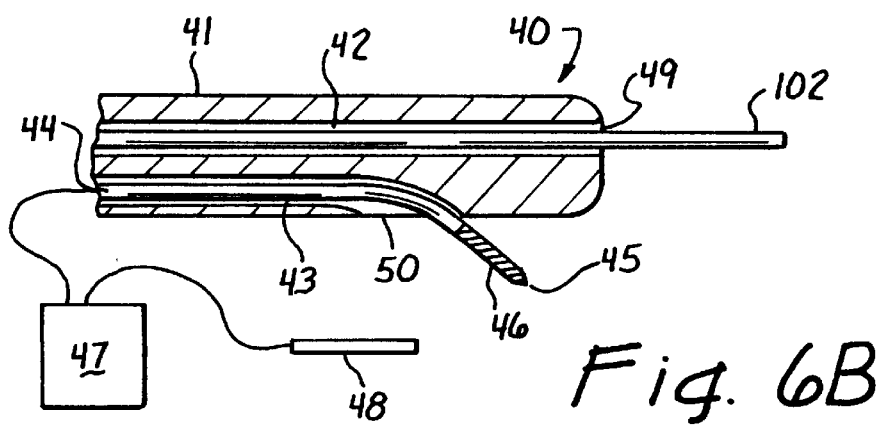

With respect to FIGS. 5A to 5C and 6A and 6B, illustrative components of the apparatus of the present invention are described. This apparatus generally includes: a plug for partially or completely occluding the coronary ostium or a segment of the venous vasculature (FIGS. 5A–5C) and a series of devices for forming veno-ventricular passageways of a predetermined size and number (FIGS. 6A and 6B).

Referring now to FIGS. 5A to 5C, three alternative embodiments of plug 14 of FIG. 4 are described. In FIG. 5A, the plug comprises cylinder 16 of open-cell, high durometer, foam. The foam may be compressed and inserted within a sheath (not shown) for delivery into the coronary sinus or a cardiac vein. Once positioned in the vessel, the sheath is withdrawn, and the foam is permitted to resume its expanded shape. Because the foam has an open-cell structure, it is expected that initially some blood will pass through the structure. It is further expected, however, that over a period of time, e.g., a few hours, days, weeks or longer, the open-cell foam will clog and clot off, thereby progressively occluding the vessel. This is expected to provide a beneficial effect in that the heart has a period of time over which to accommodate the redistribution of flow, for example, through the lymphatic system and Thebesian veins.

In FIG. 5B, an alternative embodiment of the plug is depicted, in which a layer of open-cell foam 18 of high durometer is affixed to the exterior of a previously known stent 20, such as those described in U.S. Pat. No. 4,733,665 to Palmaz or U.S. Pat. No. 5,443,500 to Sigwart et al. Stent 20 of FIG. 5B preferably is positioned in the coronary sinus or a cardiac vein, and then expanded by a conventional dilatation device (not shown) so that the open-cell foam 18 engages the wall of the vessel. Lumen 22 through the center of stent 20 may then be adjusted (either by permanent deformation in the Palmaz-type stent, or a ratcheting effect of the teeth in the Sigwart-type stent) to regulate the flow through the stent. Like the embodiment of FIG. 5A, foam portion 18 of the plug of FIG. 5B is expected to clot off after a period of time, thereby providing a gradual increase in the backpressure experienced in the venous system.

In FIG. 5C, plug 24 is formed in-situ from a biocompatible polymeric material, e.g., collagen or hydrogel, to occlude the vessel after the veno-ventricular passageways have been formed. Suitable polymers for forming such in-situ biocompatible plugs are described, for example, in U.S. Pat. No. 5,752,974 to Rhee et al, which is incorporated herein by reference.

Referring now to FIG. 6A, the distal end of device 30 suitable for forming a transmural passageway from the venous system to a cardiac chamber is described. Device 30 comprises catheter 31 having lumens 32 and 33 and preferably is constructed of biocompatible materials typically employed in catheter construction, e.g., polyvinyl chloride or polyethylene. Lumen 32 extends from the proximal end (i.e., outside the patient) to the distal end of the catheter, and includes outlet 34 in the distal endface of catheter 31. Lumen 32 accepts guidewire 101 along which catheter 31 may be advanced. Lumen 33 extends from the proximal end to the distal end of catheter, and exits through opening 35 in the lateral wall of catheter 31. Lumen 31 is sized to accept a plurality of stylets 36 having sharpened tip 37 and various diameters D. Stylets 36 preferably comprise a metal or metal alloy, such as stainless steel or a nickel-titanium alloy.

Device 30 is employed as follows: Once catheter 31 is positioned at a desired location in the venous system (i.e., the coronary sinus, great cardiac vein or other vein), stylet 36 is advanced through lumen 33 so that tip 37 exits through opening 35, punctures the myocardium, and enters the cardiac chamber. In the embodiment of FIG. 6A, stylet 36 is then withdrawn, and a stylet having a larger diameter D is then advanced through lumen 35 to increase the diameter of the transmural passageway. Once a passageway is formed, stylet 36 is withdrawn and the distal end of the catheter advanced to another location for the process to be repeated.

To assist the clinician in determining the placement, size and number of the veno-ventricular passageways to be formed, guidewire 101 may be removed once the distal end of catheter 30 is in position, and a proximal end of lumen 32 may be coupled to a pressure transducer and pressure monitoring system, as are conventionally used in cardiac bypass surgery. The pressure monitoring system is preferably programmed to compute and display a parameter such as peak pressure, mean pressure, or dP/dt. In this manner, the clinician can determine various pressure-related parameters, for example the peak pressure attained in the venous system, during the process of forming the veno-ventricular passageways. Accordingly, the clinician can adjust a planned procedure for forming a series of veno-ventricular passageways responsive to the instantaneous pressure readings attained during the procedure.

In accordance with one aspect of the present invention, a parameter associated with the pressure attained in the venous system, caused by flow through the veno-ventricular passageway, may be controlled as a function of the placement, size and/or number of passageways formed. This parameter may include, for example, peak pressure, mean pressure or rate of change of the pressure with respect to time (dP/dt). Accordingly, a variety of stylets 35, each having a progressively larger diameters, preferably are available to the clinician to form the passageway to a desired size.

Alternatively, a series of adjacent passageways may be formed, and the flow thus controlled as a function of the aggregate cross-sectional area of the passageways. As a still further alternative, the placement of the veno-ventricular passageways may be selected to ensure, for example, that a peak pressure attained in the venous vasculature does not exceed a predetermined value, for example, by adjusting the spacing between the veno-ventricular passageways.

In addition, once the clinician has completed forming one or more veno-ventricular passageways, catheter 30 may be withdrawn to a position proximal of the edge of the passageways). The clinician then may inject a suitable biocompatible polymer to form a partial or complete plug in the vessel proximal of the one or more passageways, thereby segmenting flow through the vessel.

In FIG. 6B, the distal end of an alternative embodiment of a device suitable for forming a transmural passageway from the venous system to the cardiac chamber is described. Device 40 comprises catheter 41 having lumens 42 and 43, stylet 44 having sharpened tip 45 and electrode 46, and controller 47 including a source of radio-frequency ("RF") energy. Ground plate 48 is coupled to controller 47 to complete the monopolar circuit.

Catheter 41 preferably is constructed of biocompatible materials typically employed in catheter construction, e.g., polyvinyl chloride or polyethylene. Lumen 42 extends from the proximal end (i.e., outside the patient) to the distal end of the catheter, and includes outlet 49 in the distal endface of catheter 41. Lumen 42 accepts guidewire 102 along which catheter 41 may be advanced. Lumen 43 extends from the proximal end to the distal end of catheter, and exits through opening 50 in the lateral wall of catheter 41.

Stylet 45 includes electrode 46 that forms part of a monopolar RF circuit. Electrode 46 is preferably long enough to contact the tissue along the length of a transmural channel. When energized by controller 47, electrode 46 causes a controlled degree of necrosis in the tissue surrounding the electrode. Because tissue coagulated using RF energy typically shrinks when heated, stylet 45 may be used to form a passageway having a diameter selected from a range of possible diameters. Stylet 45 and controller 47 may alternatively be configured to operate in a bipolar mode by including an additional electrode (not shown) on stylet 45.

Device 40 and stylet 45 are employed as follows: Once catheter 41 is positioned at a desired location in the venous system (i.e., the coronary sinus, great cardiac vein or other vein), stylet 45 is advanced through lumen 43 so that tip 46 exits through opening 50, punctures the myocardium, and enters the cardiac chamber. Controller 47 is then activated to coagulate a depth of tissue surrounding electrode 46, wherein the diameter of the passageway corresponds to the depth of necrosis in the tissue surrounding the electrode. Advantageously, it is expected that by coagulating the tissue a layer scar tissue will form along the interior surface of the passageway, thereby retaining the patency of the passageway.

Stylet 45 periodically may be withdrawn from the passageway during the foregoing process so that local pressure measurements may be made, for example using a pressure transducer coupled to a proximal end of lumen 42. Once a passageway of desired size is formed, stylet 45 is withdrawn and the distal end of the catheter advanced to another location for the process to be repeated. In addition, when formation of one or more veno-ventricular passageways have been formed in a segment of a vessel, the vessel optionally may be partially or completely occluded using one of the plugs described hereinabove with respect to FIGS. 5A to 5C.

Devices 30 and 40 are merely illustrative of the types of devices that may be advantageously employed to form the veno-ventricular passageways, and other instruments including a distal end effector capable of penetrating the cardiac wall may be used. For example, device 30 may alternatively include a laser cutting tip, as described, for example, in U.S. Pat. No. 5,104,393, which is incorporated herein by reference, or a mechanical cutting element, such as a rotating blade.

Figure 7A:
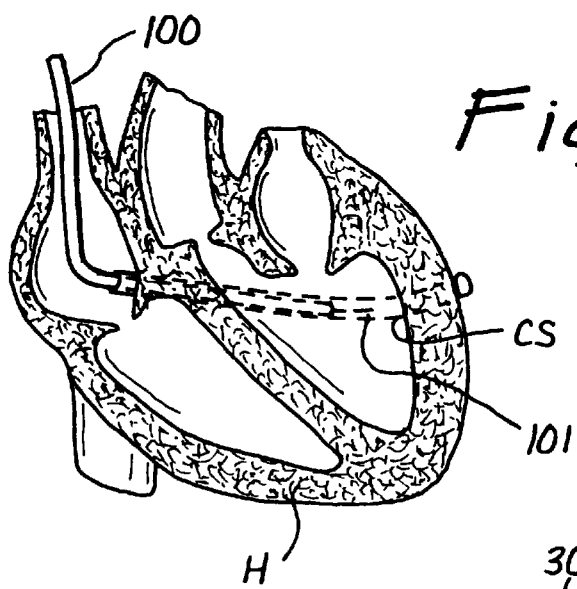
FIGS. 7A–7C illustrate the steps of transluminally providing venous retroperfusion in accordance with the methods of the present invention.
Figure 7B:
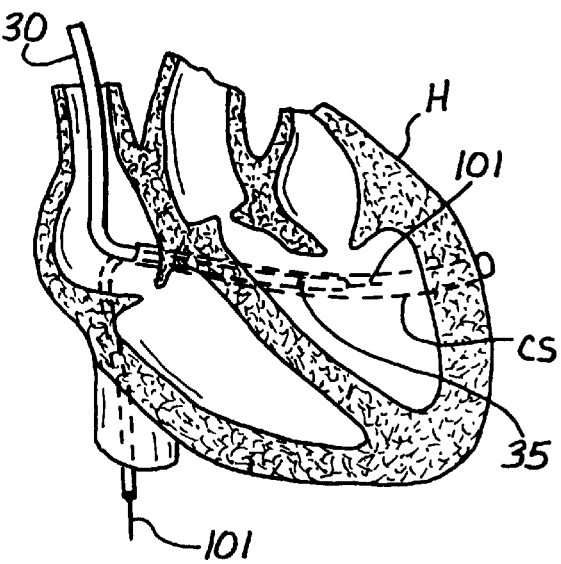
Figure 7C:
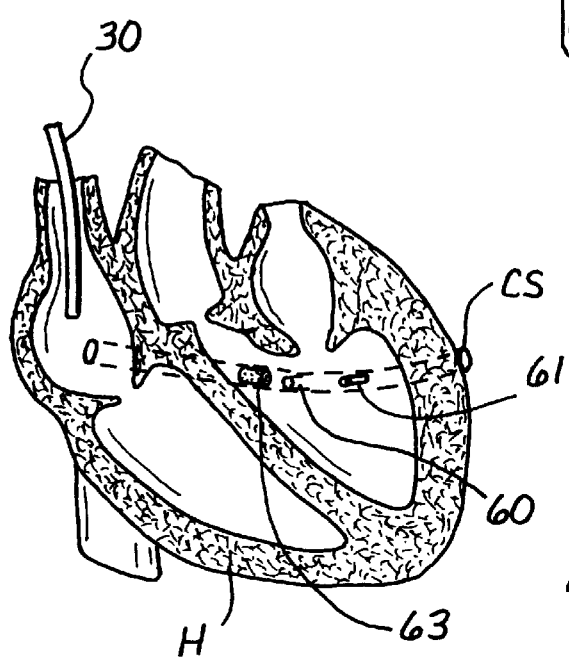

Referring now to FIGS. 7A to 7C, a method of the present invention for treating an ischemic heart of the present invention is described. Referring first to FIG. 7A, device 100 preferably comprises a previously known catheter having distally located piezoelectric ultrasound elements for mapping the coronary venous vasculature and anatomy of the adjacent cardiac chamber. Device 100 is advanced along guidewire 101 through the axillary and subclavian veins (not shown) and into right atrium RA via superior vena cava SVC.

Device 100 is then advanced through coronary ostium CO, through the coronary sinus CS, and into a desired cardiac vein, e.g., the posterior vein of the left ventricle PV. Signals generated by device 100 preferably are employed to map out the anatomy of all of the veins adjacent to the cardiac chamber. The precise spatial relationships between the coronary sinus, the cardiac veins and interior of the left ventricle may be ascertained, as illustrated, for example in FIG. 3.

Once the clinician has mapped the pertinent features of the heart, device 100 is withdrawn (with guidewire 101 is left in place) and device 30 of FIG. 6A is advanced along the guidewire, through the coronary ostium and into a selected portion of the venous system. If multiple veno-ventricular passageways are to be formed, device 30 preferably is inserted to the distal-most portion of the venous vasculature first (i.e., that furthest away from the coronary ostium).

As illustrated in FIG. 7B, stylet 36 is advanced through lumen 33 until sharpened tip 37 punctures the vessel and penetrates the myocardium into the left ventricle to form veno-ventricular passageway 60. Stylet 36 may then be withdrawn to permit the increase in venous system pressure resulting from blood passing through the veno-ventricular passageway to be measured, as described hereinabove. If the diameter of passageway 60 is such that a pressure-related metric is far below a predetermined level, a larger diameter stylet 36 may be used to enlarge veno-ventricular passageway 60. When the venous system pressure metric reaches an acceptable level (e.g., a peak pressure of 30 mm Hg), device 30 is withdrawn.

Alternatively, instead of enlarging veno-ventricular passageway 60 formed by device 30, the device may be repeatedly repositioned in the same portion of the venous vasculature to create one or more additional adjacent passageways, such as passageway 61. In this manner, the cumulative flow area into the venous vasculature may be incrementally increased so the desired pressure-related parameter reaches, but does not exceed, a predetermined level.

Referring now to FIG. 7C, if the clinician desires to employ retroperfusion in a segmental fashion, i.e., by breaking up the venous flow path into segments, optional plug 63, such as shown in FIGS. 5A to 5C, may be deployed in the cardiac vein just proximal of the veno-ventricular passageway to partially or completely occlude the vein. In this manner, the clinician may ensure that blood flow into the vein through the veno-ventricular passageway will move in a retrograde fashion through that segment of the vein. In addition, to reduce the loss of retrograde flow through the collateral veins, as described hereinafter, the coronary ostium may be either partially or fully occluded as well, or progressively occluded using the plugs described hereinabove.

Figure 8A:
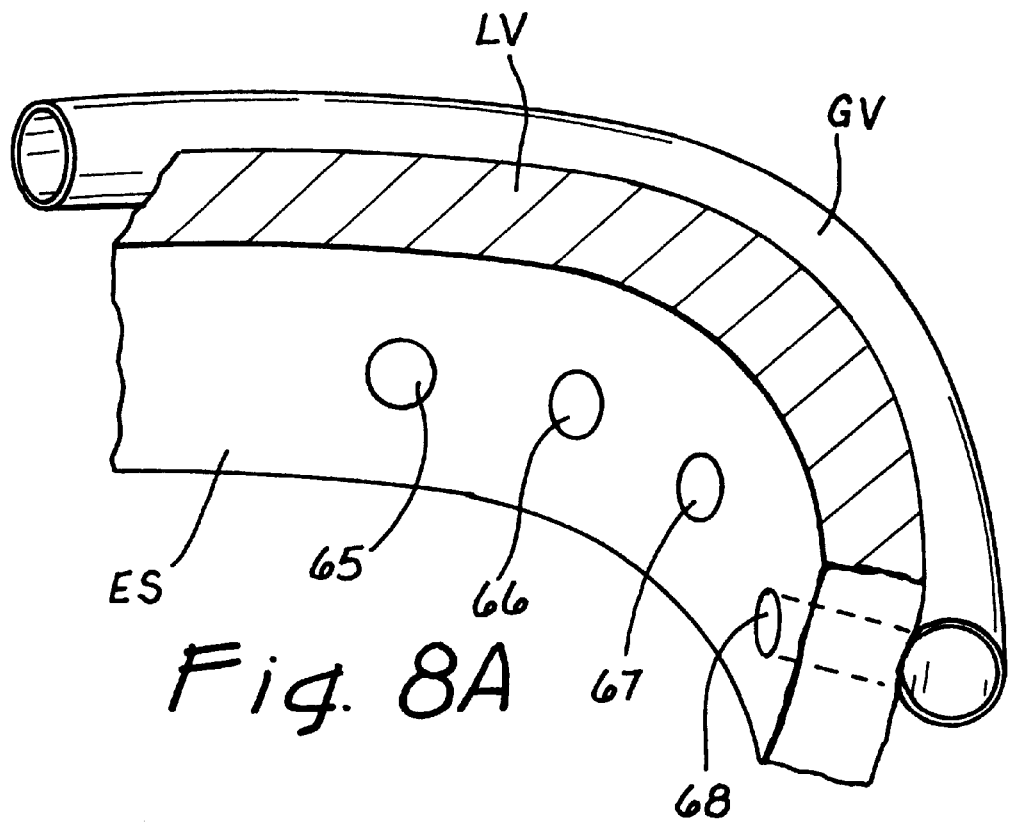
FIGS. 8A and 8B are perspective and side sectional views of a portion of a human heart showing the transmural channels formed in accordance with the present invention.
Figure 8B:
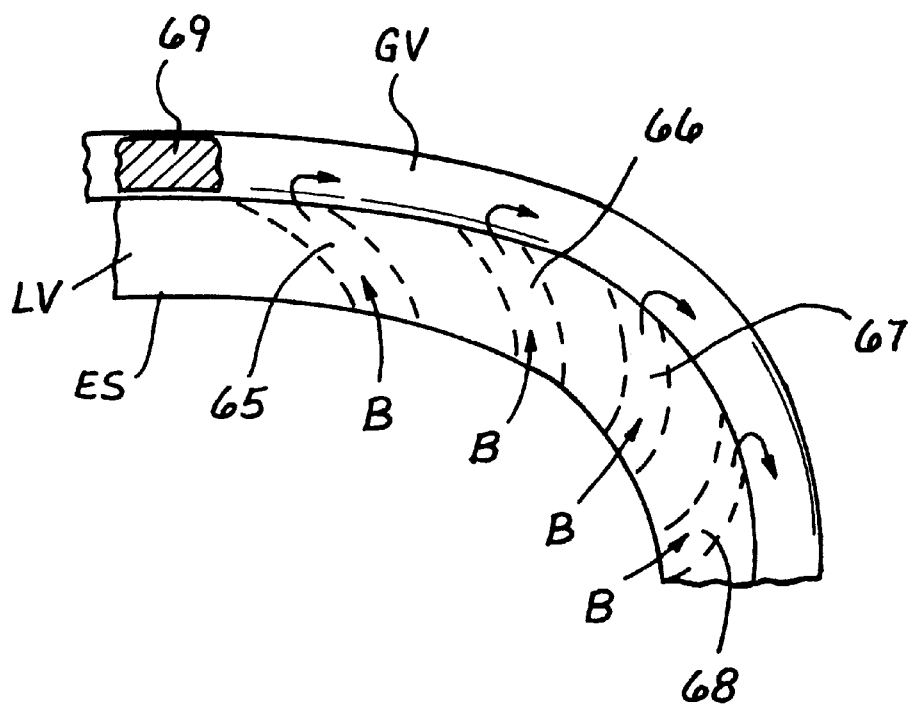

Upon completion of the foregoing steps, a number of passageways are formed between the left ventricle, and the overlying portion of the coronary sinus and cardiac veins, as depicted in FIGS. 8A and 8B. In FIG. 8A, a plurality of veno-ventricular passageways 65–68 are shown extending from endocardial surface ES of left ventricle LV into great cardiac vein GV (compare to FIG. 3). In addition, plug 69 is disposed in the vessel just proximally of veno-ventricular passageway 65 to segment that portion of great cardiac vein GV from portions closer to the coronary sinus. Arrows B in FIG. 8B illustrate the flow of blood from the left ventricle into great cardiac vein GV.

Applicants expect that a heart treated as described hereinabove can sustain chronic retrograde perfusion of the myocardium using the cardiac venous system. In addition, it is expected that the blockages within the veins and/or coronary sinus will cause a redistribution of flow within the venous system so that a greater fraction of deoxygenated blood exits via the lymphatic system and the Thebesian veins. And because the placement, size and number of the veno-ventricular passageways are selected (as well as the degree of occlusion) so that a parameter associated with the pressure in the venous system does not exceed a predetermined value, it is expected that problems associated with edema will be overcome.

Applicants further note that while the venous system is not co-extensive with the coronary arteries (particularly with respect to the right ventricle), it is nevertheless expected that the apparatus and methods of the present invention will provide relief in the majority of cases, since right ventricular infarcts are less common.

As will be apparent to one of skill in the art of cardiology, the above described apparatus may be employed in conjunction with other instruments and techniques which are per se known. For example, conventional angiographic methods may be employed to map the arterial and venous systems and the anatomy of the cardiac chamber. In addition, access to the coronary sinus may be had via the femoral veins.

Moreover, passageways between the left ventricle and the coronary sinus or cardiac veins may be created by advancing a suitable cutting instrument from within the left ventricle along the portion of stylet 35 brought out using a snare, for example, by insertion through a femoral artery, the aorta, and through the aortic valve.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. Apparatus for use in treating ischemic heart disease by providing retrograde transvenous myocardial perfusion, the apparatus comprising:

a catheter configured to be disposed in a patient's venous vasculature, the catheter having a lumen; and means for forming one or more transmural passageways between a portion of the patient's venous vasculature and a cardiac chamber so that a parameter corresponding to a peak pressure attained in the venous vasculature is less than a predetermined value.

2. The apparatus of claim 1 wherein the lumen comprises a curved portion that communicates with a skive in a lateral surface of the catheter.

3. The apparatus of claim 1 wherein further comprising means for achieving a preselected degree of occlusion of a segment of the venous vasculature.

4. The apparatus of claim 1 wherein the means for forming comprises a sharpened stylet.

5. The apparatus of claim 4 wherein the stylet further comprises an electrode for delivering RF energy.

6. The apparatus of claim 3 wherein the means for achieving a preselected degree of occlusion comprises a plug of open-cell foam having high durometer.

7. The apparatus of claim 3 wherein the means for achieving a preselected degree of occlusion comprises:

a deformable tubular member having a delivery diameter for transluminal delivery, and an expanded diameter, wherein the tubular member is deformably expanded by internal application of a radially outwardly directed force; and a layer of open-cell foam affixed to an exterior surface of the deformable tubular member.

8. The apparatus of claim 3 wherein the means for achieving a preselected degree of occlusion comprises:

a volume of biocompatible polymer that is injected to form a plug in-situ.

9. A method of treating ischemic heart disease by providing retrograde transvenous myocardial perfusion, the method comprising:

providing a catheter configured for transluminal, percutaneous insertion, the catheter having means for forming a transmural passageway in myocardial tissue;

inserting the catheter transluminally and percutaneously through a patient's coronary sinus to a position in the patient's venous vasculature; and actuating the means for forming to form a transmural passageway between the position and a cardiac chamber, the transmural passageway having a size selected to maintain a parameter related to a pressure attained in the patient's venous vasculature to a value less than a predetermined value.

10. The method of claim 9 wherein actuating the means for forming comprises actuating the means for forming to form a transmural passageway having a size selected to maintain a peak pressure attained in the patient's venous vasculature to a value less than 40 mm Hg.

11. The method of claim 9 further comprising implanting a plug in the patient's venous vasculature proximally of the transmural passageway.

12. The method of claim 9 wherein implanting a plug further comprises depositing a volume of bio-compatible polymer that forms a plug in-situ.

13. A method of treating ischemic heart disease by providing retrograde transvenous myocardial perfusion, the method comprising:

providing a catheter configured for transluminal, percutaneous insertion, the catheter having means for forming a transmural passageway in myocardial tissue;

inserting the catheter transluminally and percutaneously through a patient's coronary sinus to a position in the patient's venous vasculature;

actuating the means for forming to form a transmural passageway between the position and a cardiac chamber, the position at which the transmural passageway is formed being selected to maintain a parameter related to a pressure attained in the patient's venous vasculature to a value less than a predetermined value.

14. The method of claim 13 wherein inserting the catheter comprises inserting the catheter to a position selected to maintain a peak pressure attained in the patient's venous vasculature to a value less than 40 mm Hg when the transmural passageway is formed.

15. The method of claim 13 further comprising implanting a plug in the patient's venous vasculature proximally of the transmural passageway.

16. The method of claim 15 wherein implanting a plug further comprises depositing a volume of bio-compatible polymer that forms a plug in-situ.

17. A method of treating ischemic heart disease by providing retrograde transvenous myocardial perfusion, the method comprising:

(a) providing a catheter configured for transluminal, percutaneous insertion, the catheter having means for forming a transmural passageway in myocardial tissue;

(b) advancing the catheter transluminally and percutaneously through a patient's coronary sinus to a position in the patient's venous vasculature;

(c) actuating the means for forming to form a transmural passageway between the position and a cardiac chamber; and (d) repeating (b) and (c) at a plurality of positions to form a number of transmural passageways, the number of transmural passageways selected to maintain a parameter related to a pressure attained in the patient's venous vasculature to a value less than a predetermined value.

18. The method of claim 17 wherein repeating (b) and (c) comprises repeating (b) and (c) to form a number of transmural passageways selected to maintain a peak pressure attained in the patient's venous vasculature to a value less than 40 mm Hg.

19. The method of claim 17 further comprising implanting a plug in the patient's venous vasculature proximally of at least one of the number of transmural passageways.

20. The method of claim 19 wherein implanting a plug further comprises depositing a volume of bio-compatible polymer that forms a plug in-situ.

* * * * *